(12) United States Patent
Towe

(10) Patent No.: US 8,909,343 B2
(45) Date of Patent: *Dec. 9, 2014

(54) SYSTEMS, AND METHODS FOR NEUROSTIMULATION AND NEUROTELEMETRY USING SEMICONDUCTOR DIODE SYSTEMS

(75) Inventor: Bruce C. Towe, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/321,770

(22) PCT Filed: May 21, 2010

(86) PCT No.: PCT/US2010/035753
§ 371 (c)(1),
(2), (4) Date: Apr. 5, 2012

(87) PCT Pub. No.: WO2010/135634
PCT Pub. Date: Nov. 25, 2010

(65) Prior Publication Data
US 2012/0197342 A1 Aug. 2, 2012

Related U.S. Application Data

(60) Provisional application No. 61/180,549, filed on May 22, 2009.

(51) Int. Cl.
*A61N 1/372* (2006.01)
*A61N 1/08* (2006.01)
*A61N 1/06* (2006.01)
*A61N 1/36* (2006.01)
*A61N 1/378* (2006.01)

(52) U.S. Cl.
CPC .............. *A61N 1/06* (2013.01); *A61N 1/37223* (2013.01); *A61N 1/3605* (2013.01); *A61N 1/378* (2013.01)
USPC ..................... 607/45; 607/60; 607/48; 607/72

(58) Field of Classification Search
USPC .......................................................... 607/45
See application file for complete search history.

(56) References Cited

U.S. PATENT DOCUMENTS 4,057,069 A * 11/1977 Dorffer et al. .................. 607/61
2002/0169354 A1* 11/2002 Munro, III ......................... 600/3

(Continued)

FOREIGN PATENT DOCUMENTS

WO      WO-03/107372     * 12/2003 ............ H01H 57/00

OTHER PUBLICATIONS

Glenn et al., "Electrical Stimulation of Excitable Tissue by Radio-Frequency Transmission," *Annals of Surgery*, Sep. 1954, vol. 150, No. 3, pp. 338-350.

(Continued)

*Primary Examiner* — Carl H Layno
*Assistant Examiner* — Erin Piateski
(74) *Attorney, Agent, or Firm* — Fulbright & Jaworski LLP

(57) ABSTRACT

Methods and systems for neurostimulation and/or neurotelemetry of electrically-excitable biological tissue. Embodiments include implanting single or multiple semiconductor diodes and applying a high frequency electrical volume current. Neurostimulation embodiments include local rectification of the volume current by the diode, which can provide a pulsating electrical waveform capable of locally stimulating neural tissue, hi neurotelemetry embodiments, semiconductor diodes can be placed in contact with excitable tissue and a low level electrical carrier wave can be passed through the tissue and implanted diode whereby low level tissue bioelectric events intermodulate with the carrier wave and encode bioelectrical effects. Remote detection and amplitude demodulation of the volume-conducted carrier wave can allow recovery of the bioelectrical waveform and provide a neurotelemetry function, hi other embodiments, implanted diodes are placed in series with a pressure switch or piezoelectric material which enables their function only with the focal application of an acoustic pressure wave. This enables a selectivity amongst multiple diode channels by acoustic wave focusing or alternately by a process of range-gating of a surface applied electrical current to the arrival time of an acoustic wave at a particular device.

16 Claims, 8 Drawing Sheets

(56) References Cited

U.S. PATENT DOCUMENTS

| | | | |
|---|---|---|---|
| 2006/0079936 A1* | 4/2006 | Boveja et al. | 607/2 |
| 2006/0161225 A1* | 7/2006 | Sormann et al. | 607/61 |
| 2006/0167500 A1* | 7/2006 | Towe et al. | 607/3 |
| 2007/0185551 A1 | 8/2007 | Meadows et al. | 607/61 |
| 2007/0293910 A1 | 12/2007 | Strother et al. | 607/48 |
| 2008/0188909 A1 | 8/2008 | Bradley | 607/59 |
| 2008/0208293 A1* | 8/2008 | Parramon et al. | 607/61 |
| 2008/0215112 A1* | 9/2008 | Firlik et al. | 607/45 |
| 2008/0306359 A1* | 12/2008 | Zdeblick et al. | 600/302 |

OTHER PUBLICATIONS

Heetderks, "RF Powering of Millimeter- and Submillimeter-Sized Neural Prosthetic Implants," *IEEE Transactions on Biomedical Engineering*, vol. 35, No. 5, pp. 323-327. May 1988.

Matthaei "A Study of the Optimum Design of Wide-Band Parametric Amplifiers and Up converters Up Converters," *IRE Transactions on Microwave Theory Tech.*, vol. MTT-10, pp. 23-38, Jan. 1961.

Moheseni et al., "Wireless Multichannel Biopotential Recording Using an Integrated Fm Telemetry Circuit," *IEEE Transactions on Neural Systems and Rehabilitation Engineering*, vol. 13, No. 3, pp. 263-271, Sep. 2005.

PCT International Preliminary Report issued in International Application No. PCT/US2010/035753, dated Dec. 1, 2011.

PCT International Search Report and Written Opinion t issued in International Application No. PCT/US2010/035753, dated Jan. 18, 2011.

Sard et al., "A positive resistance up-converter for ultra-low noise amplification," *IEEE Trans. Micro Theory Tech.*, vol. 14, pp. 608-618, Dec. 1966.

Towe "Passive Biotelemetry by Frequency Keying," *IEEE Transactions on Biomedical Engineering*, vol. BME-33, No. 10, pp. 905-909, Oct. 1986.

Wise et al., "Wireless Implantable Microsystems: High-Density Electronic Interfaces to the Nervous System," *Proceedings of the IEEE*, vol. 92, No. 1, pp. 76-97, Jan. 2004.

* cited by examiner

SYSTEMS, AND METHODS FOR NEUROSTIMULATION AND NEUROTELEMETRY USING SEMICONDUCTOR DIODE SYSTEMS

STATEMENT OF GOVERNMENT SUPPORT

This invention was made with government support under R21 NS063213 awarded by the National Institutes of Health. The government has certain rights in the invention.

This application is a national phase application under 35 U.S.C. §371 of International Application No. PCT/US2010/035753 filed May 21, 2010, which claims priority to U.S. Provisional Patent Application Ser. No. 61/180,549 filed May 22, 2009. The entire text of each of the above-referenced disclosures is specifically incorporated herein by reference without disclaimer.

BACKGROUND

1. Technical Field

This invention relates to methods of stimulating and recording from the nervous and muscular system of the human body through the use of implantable devices based on semiconductor diodes.

2. Description of Related Art

There is interest in methods of directly stimulating bioelectrically excitable tissues by artificial means since this allows their function to be evoked or modified, thus providing a therapeutic or otherwise desirable biological effect. For example, neurostimulation may be used for restoring function in cases of neural injury or disease. Neurostimulation in this context refers to the stimulation of electrically excitable tissues of living things. This can include, for example, the human tissues of the brain, heart, muscle, and nervous system.

There is also interest in recording tissue bioelectrical events. Tissue bioelectrical events arise from the flow of ionic currents as a result of the action of cellular ionic pumps and channels, which underlie the bioelectrical activity of neural and muscle tissues in the body. These neural and muscle tissues are associated with the function of the brain, muscles, and nervous system. The ionic currents are well known and are used for electro-cardiograms, electroneurograms, and electromyograms.

A common method of neurostimulation is the application of pulsed electrical currents directly to tissue through electrodes implanted within tissue or indirectly through the body surface.

Electrical currents applied to tissue are known to affect the membranes of excitable cells, causing a depolarizing effect that can lead to a cell action event that depends on its type and biological function. The pulsing of currents is needed to prevent accommodation to current flows and to fulfill certain physiologic conditions that enables electricity to be effective.

It is also possible to apply electrical currents to the body surface in which case they diffuse in the volume conductivity of tissue and attenuate according to well known laws. These currents can also stimulate near-surface nerves and muscle tissues to some degree. but cannot reach deeper tissues because of high electrical losses in tissue and the rise in the needed current levels to above those that would cause electrical shock.

The strong diffusion of electrical current in tissues from surface electrodes means that specific stimulation of a given nerve or nerve fiber within a bundle is very difficult and rather there is a tendency for electrical currents applied to the body surface to broadly stimulate in undesirable ways. Implantable electrodes overcome these problems but are invasive and suffer from the undesirable need to either run wires through the skin or work with relatively bulky implanted power systems that run on batteries or are powered by external radiofrequency (RF) powering techniques.

Technologies that deliver electrical currents to tissues by way of RF induction to an implanted device are well known to the art. In general these approaches use an inductor implanted within the body to magnetically couple to an external RF field. Often times this inductor is coupled with a capacitor to form a resonant circuit that is more efficient in coupling to applied RF energy. These devices are relatively large and can be on the order of a centimeter in size. A discussion of methods of coupling energy to implanted RF devices was published by Heetderks (1988) and an overview of the current state of the art and sizes of neuroimplants by Wise et al. (2004) and by others is incorporated herein by reference. The Heetderks paper mostly confines itself to power induction at frequencies below about 50 MHz. The inventors find however that higher frequencies in the hundreds of megahertz and into the microwave region above about 500 MHz are also being used in some designs.

High frequency currents are not known to stimulate bioelectrically excitable tissues of the nervous system of the body because they are faster than physiologic events can respond. As long as they are relatively high frequency, above several tens of kilohertz and continuing up into the megahertz region currents do not stimulate bioelectrical events or sensations of pain.

A major concern in the development of neurostimulators for implantation near nerve or muscle for therapeutic applications in the human body is the size of the implant. It is preferable that the implanted devices be small and perhaps something that could be introduced into the body through minimally invasive methods, such as syringe needle injection. This is not only for ease of insertion into tissues, but so that they produce less complications such as pressure or force against sensitive tissues as a person moves or exercises. There is also less immunological response and inflammation of tissues with small devices as it reduces their attendant risk of complications. This feature tends to encourage more widespread use in situations which are elective rather than critical.

A neurostimulation device known as a Bion™ has been described by Loeb et al. which is an example of present methods of designing implantable neurostimulation devices. It is a small cylindrical electrical device which derives its energy from an externally applied RF field. As presently designed, the size of these devices ranges from 6 mm to about 1.5 cm. These devices incorporate active LSI logic and inductive RF powering.

Some versions store energy in batteries or capacitors to deliver later upon digital command and so provide electrical pulses through integral electrodes to neural tissues. These devices are targeted for therapeutic stimulation of muscle and nerves by being implanted within body tissues and in some cases are used for pain relief, treating urinary incontinence, and can be programmed to actuate nerves and muscles in the restoration of lost function in limbs. A disadvantage of these devices is their relative complexity and large size. The large size limits their medical applicability to situations where they can be introduced by surgery or through a large trocar.

This application incorporates by reference provisional patent application Nos. 60/916,152 filed on May 4, 2007 and 61/093,546 filed on Sep. 2, 2008 in their entirety.

SUMMARY

Embodiments of the present invention provide methods and systems for micro-implantable devices for neurostimulation powered by microwave range electromagnetic radiation applied to the body surface. In comparison to the use of relatively large resonant circuits and inductive transformer coupling to implanted devices, embodiments of the present invention show that single semiconductor diodes implanted into tissues, in combination with a skin-surface applied source of high frequency electromagnetic radiation in the microwave region, can cause the stimulation of neural tissue if the diode electrical contacts are electrically coupled to the tissues. In certain embodiments, the diode electrical contacts are placed in direct and implanted contact with the tissues.

Embodiments of the present invention comprise a semiconductive diode, made from conventional silicon technology as known to those in the art, implanted into tissue such that its electrical contacts are in local proximity to electrically excitable tissue (e.g., the brain, muscle, or nervous system). Electrical current flows can be induced into the volume conductivity of tissue by the antenna of a local high frequency transmitter. In certain embodiments, the transmitter is a microwave range transmitter of the type used in communications.

In other embodiments, the electromagnetic energy can be applied to the body by way of conventional bioelectrodes as known to the art such that the current path between the bioelectrodes optimally intercepts the implanted device contacts. A portion of the induced current path can be intercepted by the device and thereby rectified. The rectification at the diode can also produce a high frequency pulsating and monopolar current.

The current can be smoothed in its ripple by the capacitive nature of the electrode interface and by the cell membranes of excitable tissues. Such currents can cause action events of nerve and muscle which behave as if they were stimulated by conventional neuroelectric stimulators, including for example, neuroelectric stimulators having monophasic pulses on the order of 100 mV to 3 volts and durations on the order of tens of microseconds to several milliseconds.

This result is unexpected to those skilled in the art of neurostimulation. There is the general belief that high frequency currents provided by microwave radiation to the body, or even partially rectified, are not suited in frequency and waveform characteristics to the task of neurostimulation. Embodiments of the present invention demonstrate that this is an incorrect assumption and that high frequency pulsatile currents from a simple diode rectifying system can cause neurostimulation. Embodiments of the present invention comprise neurostimulation devices of a new principle and functionality.

Embodiments of the present invention provide the advantage of electrical simplicity compared to existing art. For example, exemplary embodiments are comprised primarily of a semiconductor diode, or small integrated network of diodes in a bridge or voltage doubler configuration, directly implanted in tissue and without the bulk or needed open-loop area of an inductive component. The diode lead wires can provide an electrical contact to tissue at their point of emergence from the insulating packaging. Short leads of millimeter-order can be used to confine currents to local excitable tissue or the fine wire insulated leads may be extended out a distance along a line to encompass the stimulation of a greater volume of tissue.

Exemplary embodiments comprise systems and methods to stimulate and record from bioelectrically excitable tissue in the human body. Embodiments comprise the introduction of semiconductor diodes into the tissue and subsequent application of high frequency electrical currents to the skin overlying that region. In certain embodiments, zero-bias Schottky diodes may be used due to their relatively lower threshold voltages and minimal electrical losses. High frequency electrical currents alone generally do not stimulate tissue but at diodes convert from the high frequency alternating current into a pulsating direct current that is effective in stimulation of excitable tissue.

This neurostimulation approach is based on the observation that relatively high values of pulsed current 10 mA and more can be passed through the human body using skin electrodes or by using noncontacting RF antennas without any sensible feeling of shock or heating. In the case of electrodes this is due to their relatively large capacitive nature that causes the current to bypass the tissue resistance. This minimizes tissue heating and with short pulses on the order of a millisecond and less means that the total average power is relatively low. With RF antennas, there is an induction of an electrical current into tissue according to well known laws of magnetic induction and of radiofrequency propagation.

Embodiments of this invention employ the recognition that a semiconductor diode placed in the current path will rectify a portion of the overall current creating a pulsatile direct current waveform known to be able to excite tissues. The ability of pulsed DC currents to neurostimulate, even at high frequencies by this method, is thought to be effective because of an integration of the current by way of the bioelectrical membrane capacity of excitable cells.

In addition embodiments of this invention also employ the recognition that relatively small electrical currents, in the tens of microampere range, can be effective in stimulating excitation. Specific embodiments utilize a diode or series of diodes intercepting and rectifying even a small part of the current flow driven by remote electrodes in tissue can act as a local generator of a waveform sufficient to stimulate tissue.

Embodiments of the present invention have the potential to provide therapeutic neurostimulation for medical applications of an unusually wide scope including, for example, Parkinson's disease, epilepsy, mental depression, obesity, incontinence, functional rehabilitation, stroke, and pain relief.

Embodiments of the present invention may also enable therapeutic medical applications not possible or practical with current medical device approaches. For example, certain embodiments may serve as a replacement for pharmaceuticals in certain applications but without the side effects of drugs. The small size of implants used in some embodiments allows syringe needle introduction to tissues, which reduces surgical trauma. Their size improves their practicality and greatly extends their range of potential clinical applications.

The term "coupled" is defined as connected, although not necessarily directly, and not necessarily mechanically. The terms "a" and "an" are defined as one or more unless this disclosure explicitly requires otherwise. The terms "substantially," "approximately," "about," and variations thereof are defined as being largely but not necessarily wholly what is specified, as understood by a person of ordinary skill in the art. In one non-limiting embodiment, the term substantially refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but it may also be configured in ways other than those specifically described herein.

DETAILED DESCRIPTION OF EXEMPLARY EMBODIMENTS

Exemplary embodiments of the present invention include systems and methods for providing neurostimulation and/or neurotelemetry to biological tissues. An overview of exemplary methods will be provided initially, followed by more detailed description of specific features of exemplary systems and methods.

Neurostimulation Embodiments

Figure 1:
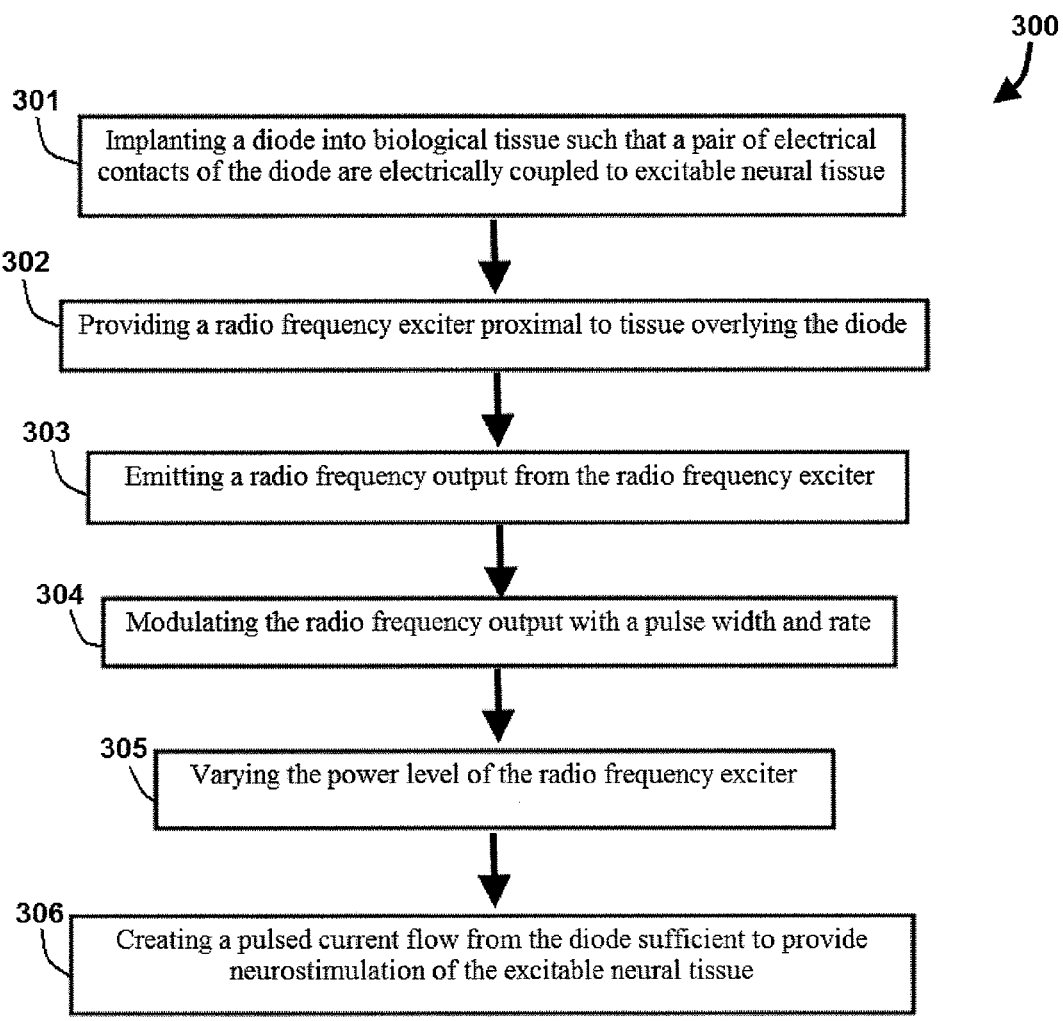
FIG. 1 is schematic flowchart diagram illustrating one embodiment of a method for providing neurostimulation.

Referring initially to FIG. 1, an exemplary method 300 of providing neurostimulation to biological tissues is shown. It is understood that while features of method 300 are shown and described in FIG. 1 as individual "steps", this embodiment is not limiting. Other embodiments may comprise different combinations of the individual features shown and described in FIG. 1 or may comprise the features in a different order than that shown in FIG. 1.

Method 300 comprises a step 301 of implanting a diode into biological tissue such that the electrical contacts of the diode are electrically coupled to excitable neural tissue. In this embodiment, method 300 also comprises a step 302 of providing a radio frequency exciter proximal to tissue overlying the diode and a step 303 of emitting a radio frequency output from the radio frequency exciter. In specific embodiments, the output from the radio frequency exciter is an electric field in the microwave range. Method 300 also comprises a step 304 of modulating the radio frequency output with a pulse width and rate and a step 305 of varying the power level of the radio frequency exciter. Furthermore, method 300 comprises a step 306 of creating a pulsed current flow from the diode sufficient to provide neurostimulation of the excitable neural tissue.

Figure 2:
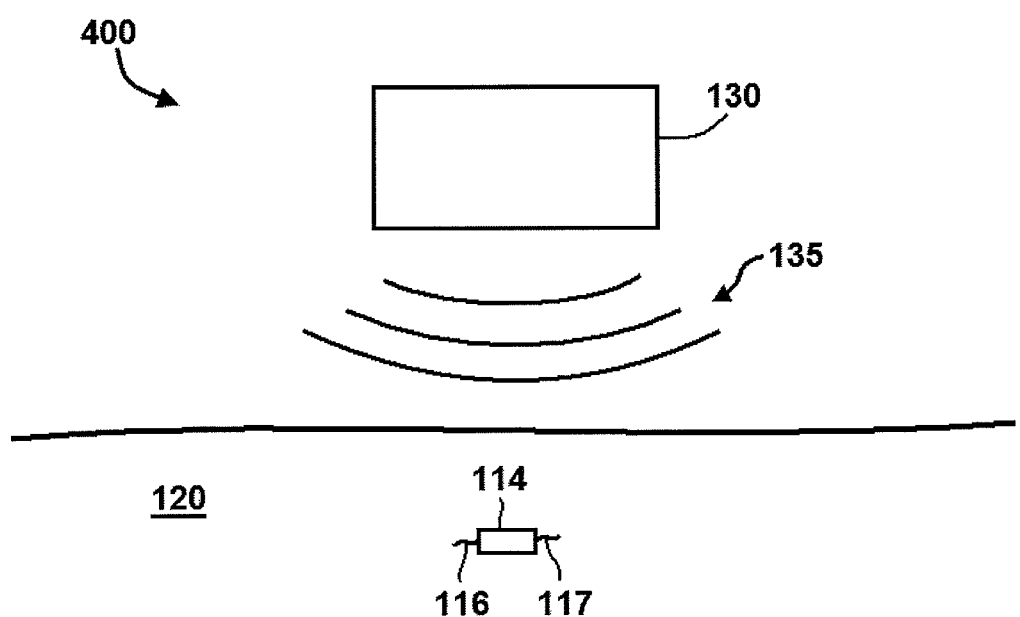
FIG. 2 is a schematic block diagram illustrating one embodiment of a system for providing neurostimulation.

Referring now to FIG. 2, a system 400 configured to provide neurostimulation comprises a diode 114 comprising a pair of electrical contacts 116 and 117. It is understood that the components shown in FIG. 2 are not drawn to scale, and that certain components may be enlarged to provide clarity in the illustration. In this embodiment, diode 114 is implanted into electrically-excitable neural tissue 120. A radio frequency exciter 130 is placed proximal to the tissue overlying diode 114 and is configured to emit a radio frequency electrical output 135. In specific embodiments, radio frequency electrical output 135 is a microwave frequency output. In particular embodiments, radio frequency electrical output 135 has a frequency between 100 MHz to 8 GHz.

During operation, radio frequency output 135 is modulated with a pulse width and rate. In specific embodiments, radio frequency output 135 is pulsed on for a time period between approximately 50 microseconds to several milliseconds. In particular embodiments, radio frequency output 135 may be pulsed between approximately once per second to two hundred times per second. This provides for a relatively low total amount of microwave energy applied to neural tissue 120.

Radio frequency output 135 is received by diode 114 and rectified so that a pulsed current flows from electrical contacts 116 and 117 sufficient to provide neurostimulation of excitable neural tissue 120. In specific embodiments, the pulsed current from electrical contacts to neural tissue 120 is between 10 microamps and 20 milliamps.

Figure 3A:
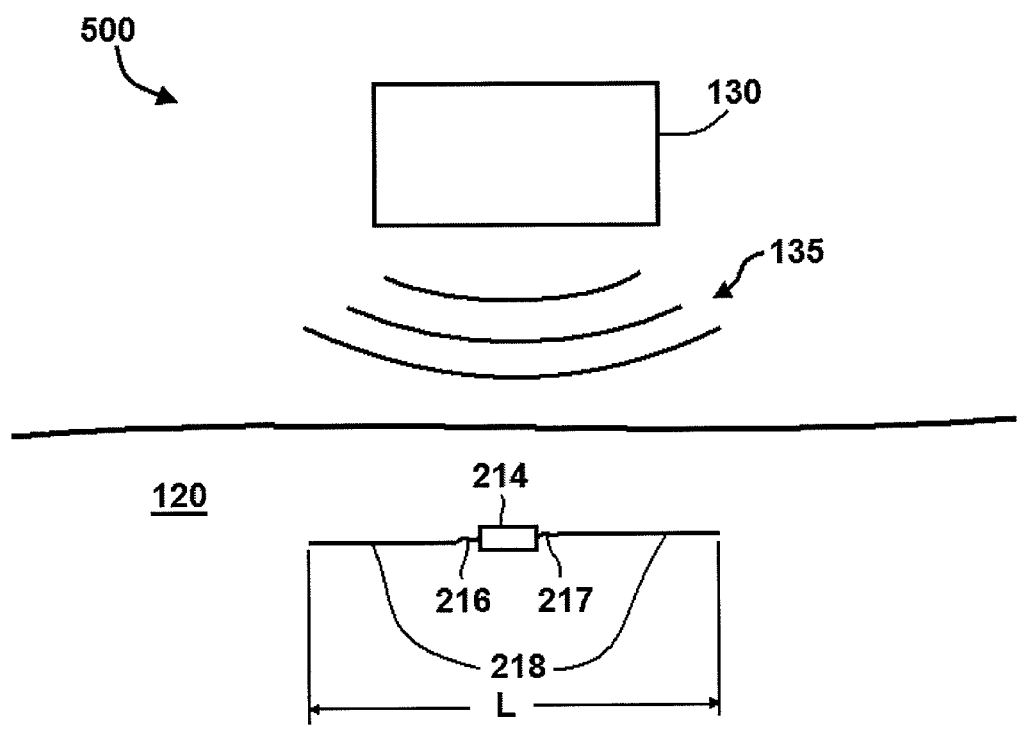
FIG. 3A is a schematic block diagram illustrating one embodiment of a system for providing neuro stimulation.
Figure 3B:
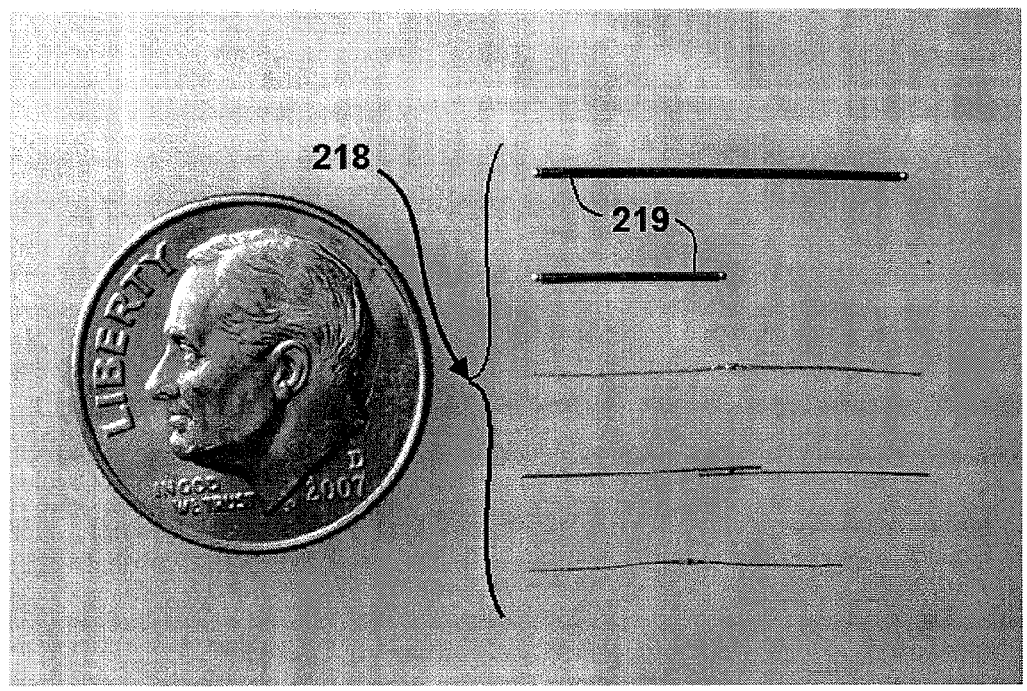
FIG. 3B is a depiction of a component of the system of FIG. 3A.

Referring now to FIG. 3A, a neurostimulation system 500 is similar to that of the previously described embodiment of FIG. 2. For example, system 500 utilizes radio frequency exciter 130 to emit a radio frequency electrical output 135. In this embodiment, however, diode electrical contacts 216 and 217 of diode 214 are coupled to a dipole 218. Dipole 218 serves as an antenna to receive radio frequency electrical output 135. In certain embodiments, dipole 218 has a length L that is between 1 millimeter and 1 centimeter. In other embodiments, dipole 218 has a length L between 1 centimeter and 5 centimeters. As shown in FIG. 3B, dipole 218 may be configured in any number of different configurations.

In certain embodiments, dipole 218 may comprise an outer casing 219 that functions as a protective shell for dipole 218 and a diode.

In certain embodiments, the intensity of microwave energy applied to the body or skin can be a factor in determining the separation distances of the diode electrical contacts (e.g., electrodes). Small diode electrode spacings can require a more localized application of microwave energy and a greater energy density. There can be a trade-off in stimulation depth versus applied microwave power with decreasing diode electrode separation distances.

Penetration depth of the microwave energy follows well known laws to those skilled in the art. In general, microwave frequencies in the UHF range to X band (8-12 GHz) have sufficient penetration depths ranging from 10 or more centimeters to a few millimeters in tissues and are so suited for embodiments of the present invention.

Microwave energy applied to the body can be focused and directed by well known techniques using reflectors, phased array systems, and similar approaches known to those skilled in the art of microwave antenna design. By incorporating these techniques, embodiments of the present invention are able to use less overall energy by focusing it towards the location of the implanted device.

Certain embodiments of the present invention may also comprise a series of implanted diodes distributed over some volume such that they intercept a greater portion of the energy transmitted by the radio frequency exciter. In specific embodiments, the diodes can be implemented in a form factor of thin needle-like configurations with the electrical contacts disposed on either end. This configuration may allow the diodes to be inserted easily into tissues while increasing the amount of energy captured when multiple diodes are used, which may increase the amount of neurostimulation Embodiments of the present invention include compact dimensions that provide benefits in installation and use of the system. For example, diodes can be manufactured in micron-order size scales by photolithographic methods well known to those skilled in the art. In exemplary embodiments, a primary limitation on implant size is the needed dipole length. For certain embodiments, the dipole length is in the range of a millimeter or so to several centimeters (e.g. between 1 centimeter and five centimeters). This length may be needed to accommodate the extent of the bioelectrical dipole stimulation length for the specific application in-vivo. In general, the higher frequencies of microwave energy, above about 1 GHz and extending to approximately 10 GHz are more desirable for diode systems that are implanted within about several millimeters to 2 cm of the surface of the body.

Figure 4:
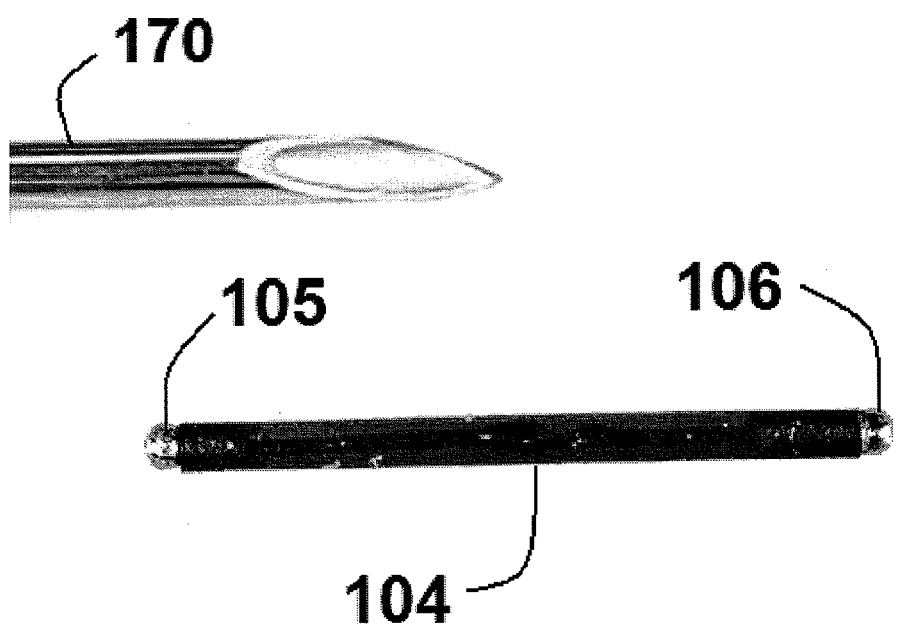
FIG. 4 is a depiction of a component used in a neurostimulation system.

Some embodiments of the present invention are reduced in physical size as compared to existing neurostimulation devices. As shown in FIG. 4, in certain embodiments, an implant 104 (which contains a diode such as diode 114 or diode 214 shown in the previous figures) is compatible with a needle 170 such as those used in common 18 gauge (or smaller) syringe used in medicine. In the embodiment shown, implant 104 also comprises a platinum electrode ball 105 at a first end of implant 104 and a platinum electrode ball 106 at a second end of implant 104.

In certain embodiments, the microwave energy applied to the body surface is generally pulsed over a relatively short interval and in the range of about 50 μs to several milliseconds and usually low duty cycles such as 10 pulses per second so that the total amount of microwave energy delivered to the body surface is relatively low. The pulse duration parameters can be defined by the needed stimulation characteristics of the neural tissue and follow well known strength-duration relationships such as those published by Reilly. The microwave pulse width and frequency in combination with the implanted diode form a system that can mimic the electrical output of a conventional wired electrical neurostimulator. In exemplary embodiments, the 1% or less pulse duty cycle means that the body tissues do not experience a thermal warming effect by application of the microwave energy to the body surface.

Figure 5:
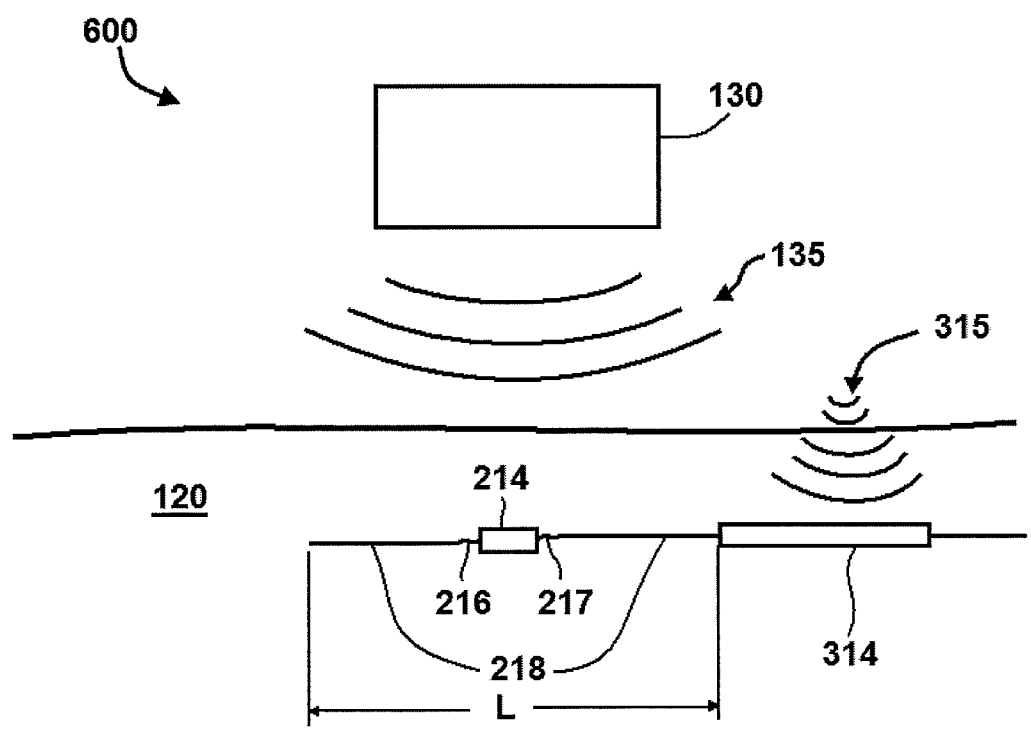
FIG. 5 is a schematic block diagram illustrating one embodiment of a system for providing neurostimulation.

In certain embodiments, the diode or diodes are placed in series or parallel with a microminiature electrical switch. In specific embodiments, the switch comprises a polymer material loaded with a finely dispersed particulate conductive phase. In such embodiments, this polymer material permits the process of electronic conduction by electron hopping (also known as percolation) that occurs when a sufficient number of conductive particles are close enough to permit electronic tunneling through the intermediate distance of insulator. Small changes in particle distance spacing by the passage of a pressure wave can effectively causes a change in the resistance of the polymer and thus accomplish the function of a switch. Referring now to FIG. 5, a system 600 comprises an implanted electrical switch 314 coupled to diode 214. Switch 314 may be configured to be activated by an acoustic pressure wave 315, so that when switch 314 is activated, diode 214 will conduct an electrical current. In other respects, system 600 is equivalent to system 500 described previously. Accordingly, other aspects of the operation of system 600 will not be described in detail.

When sound energy impacts this composite device, the resistance of the switch falls due to a pressure response and enables current to flow through the diode. This approach allows selectivity of neurostimulation between a number of diodes implanted in tissue by way of timing the electrode electrical current flow to the arrival of the sound at the diode location.

Likewise the sensitivity of a diode can be switched on and off momentarily by the passage of an acoustic pressure wave using a percolating particulate polymer. The insulating polymer should have properties of substantial resistance to the fluid medium in which it is used. This form of pressure transducer has the advantages that it can be made in very thin layers and can be disposed on a substrate by commercial processes of photolithography and batch fabrications. It has a relatively large change in current flow with pressure and can be used with small exposed polymer areas and so lending itself to miniaturized sensors.

Neurotelemetry Embodiments

Embodiments utilizing multiple diodes can be utilized to perform various functions. For example, recording of the spontaneous activity of the nervous system is of high interest in the design of neuroprostheses and in creating effective methods of using electrical stimulation to replace lost function. The creation of man-machine interfaces requires ways of detecting neural activity of the body as well as stimulating it. Thus, there is interest in designing systems that not only stimulate excitable tissue but record from it and that then can provide a function of telemetry of signals from within the body to the skin surface where they can be telemetered to a remote location.

In certain embodiments, locating or implanting semiconductor diodes near electrically active neural tissues can provide a telemetry function. This function can allow a recording of the bioelectrical events in body tissue by recording and demodulating signals that result from the interaction of bioelectrical currents with a high frequency driven carrier current passing through a semiconductor diode whose leads contact tissue.

The human body can be electrically modeled as a volume conducting medium. Natural or artificial current sources in the interior of the body will thereby produce volume potentials. Bioelectrical currents flowing in excitable tissue in the body are generally modeled as current sources in the range of tens to hundreds of microamperes and with associated electric fields in the range of microvolts to tens of millivolts in the case of transmembrane potentials. These devices can be understood from volume conductor propagation of a small dipolar current source in tissue that follows well understood rules. The potential V appears on the skin surface as:

$$V = id \cos \theta / 4\pi\sigma r^2$$

Where i is the current flow over a dipole length d, σ is the medium conductivity, and r is the distance from the center of the dipole to the skin surface. Thus there is a square law loss of the signal strength generated by the current source at depth from the body surface and there is a vector relationship to orientation of the electrode pairs.

An unexpected principle noted in exemplary embodiments of the present invention is that low level bioelectrical events can alter the characteristics of RF semiconductor junction diodes in a way that is remotely detectable without the necessary use of biopotential preamplification.

The characteristics of p-n junction diodes, such as those that may be suitable for diode 114 or 214 in previously-described embodiments, can be substantially varied in their characteristics by biopotentials when reverse biased or when biased near their turn-on threshold. Parameters such as junction capacitance, effective resistance, and nonlinear second harmonic production can all be substantially affected by sub-millivolt level electrical signals applied to them.

Figure 6:
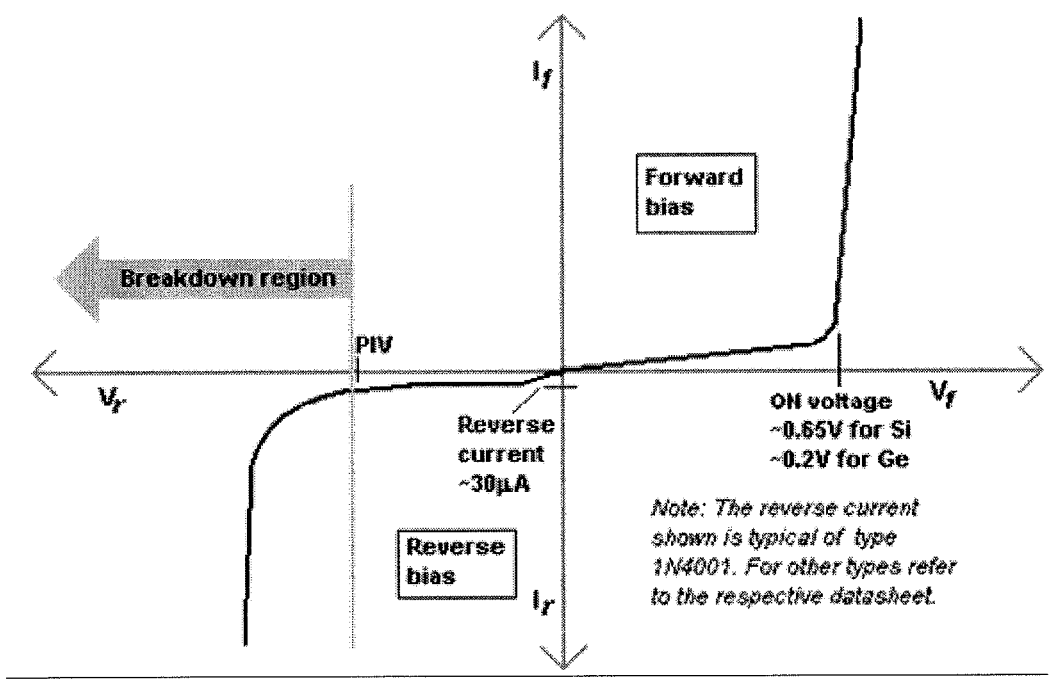
FIG. 6 is a graph illustrating a voltage response of a diode in accordance with the present embodiments.

This process can be conceived as the diode acting as a (nonlinear) multiplying element. The Shockley equation shows the relationship of the diode forward current to an applied bias voltage.

$$I=I_S(e^{V_D/(nV_T)}-1)$$

where I is the diode current, $I_S$ is a scale factor called the saturation current, $V_D$ is the voltage across the diode, $V_T$ is the thermal voltage, and n is the emission coefficient. FIG. 6 shows the sharp knee in the i-v curve near on threshold. By operating $V_D$ slightly below this point (which moves towards the origin in zero-bias type Shottky diodes) millivolt biopotential signals can amplitude modulate an externally applied and relatively high frequency carrier current also passing through the diode. This process is known as mixing or sometimes as intermodulation when applied to the design of radio devices. This process may be performed using high performance low-noise mixer diodes, such as those that are routinely used in RF communications at microvolt signal levels. Accordingly, in such an embodiment, the mixing process may not be a significant source of noise or limitation on the biopotential intermodulation process.

Figure 7:
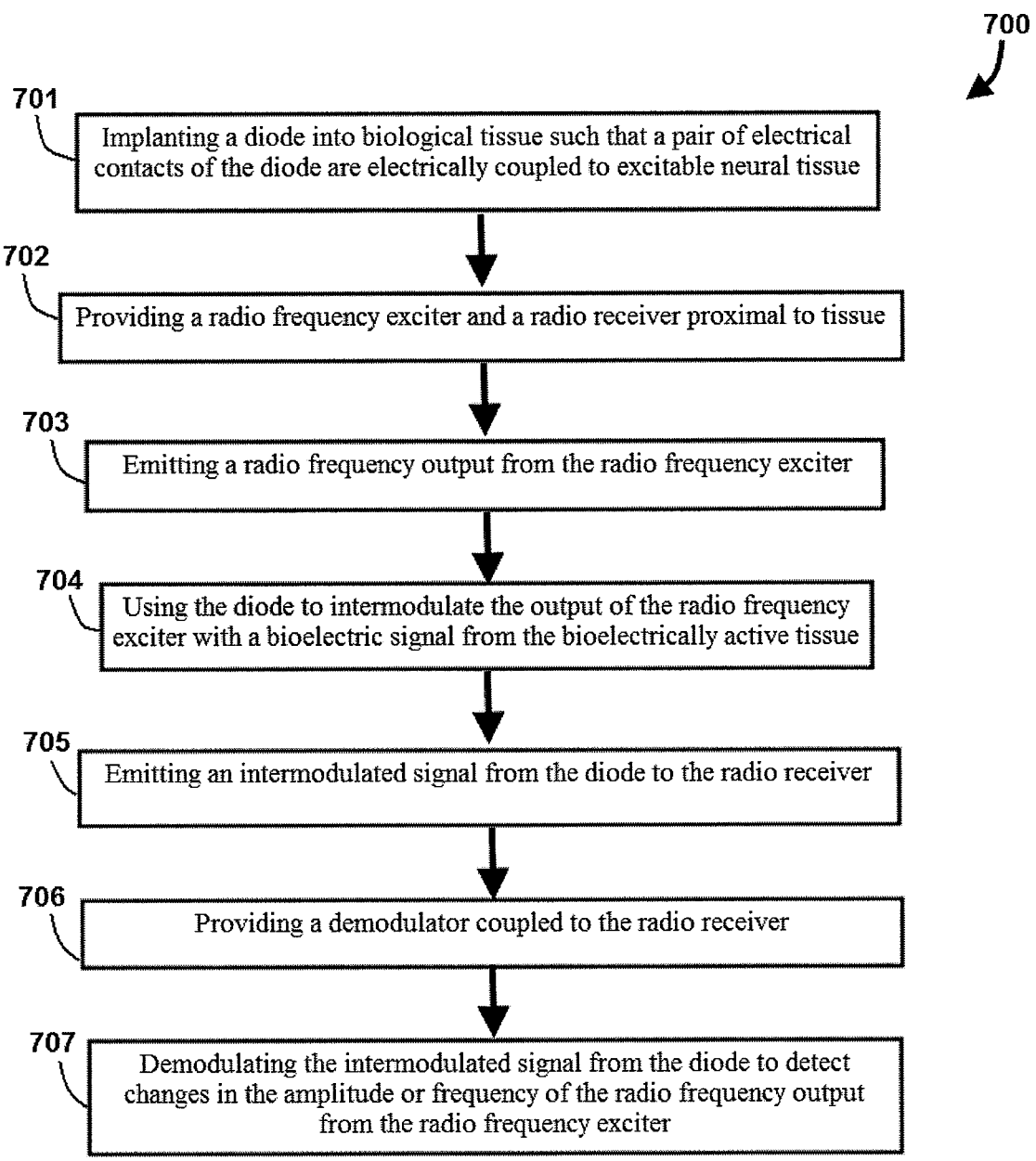
FIG. 7 is schematic flowchart diagram illustrating one embodiment of a method for providing neurotelemetry.

Referring now to FIG. 7, an exemplary method 700 of providing neurotelemetry from biological tissues is shown. It is understood that while the features of method 700 are shown and described in FIG. 7 as individual "steps", this embodiment is not limiting. Other embodiments may comprise different combinations of the individual features shown and described in FIG. 7 or may comprise the features in a different order than that shown in FIG. 7.

The exemplary embodiment illustrated in method 700 comprises a step 701 of implanting a diode proximal to bioelectrically active tissue and a step 702 of providing a radio frequency exciter and a radio receiver proximal to tissue overlying the diode. Method 700 further comprises a step 703 of emitting a radio frequency output from the radio frequency exciter to the diode and a step 704 of using the diode to intermodulate the output of the radio frequency exciter with a bioelectric signal from the bioelectrically active tissue. Method 700 additionally comprises a step 705 of emitting an intermodulated signal from the diode to the radio receiver and a step 706 of providing a demodulator coupled to the radio receiver. Furthermore, method 700 comprises a step 707 of demodulating the intermodulated signal from the diode to detect changes in the amplitude or frequency of the radio frequency output from the radio frequency exciter.

Figure 8:
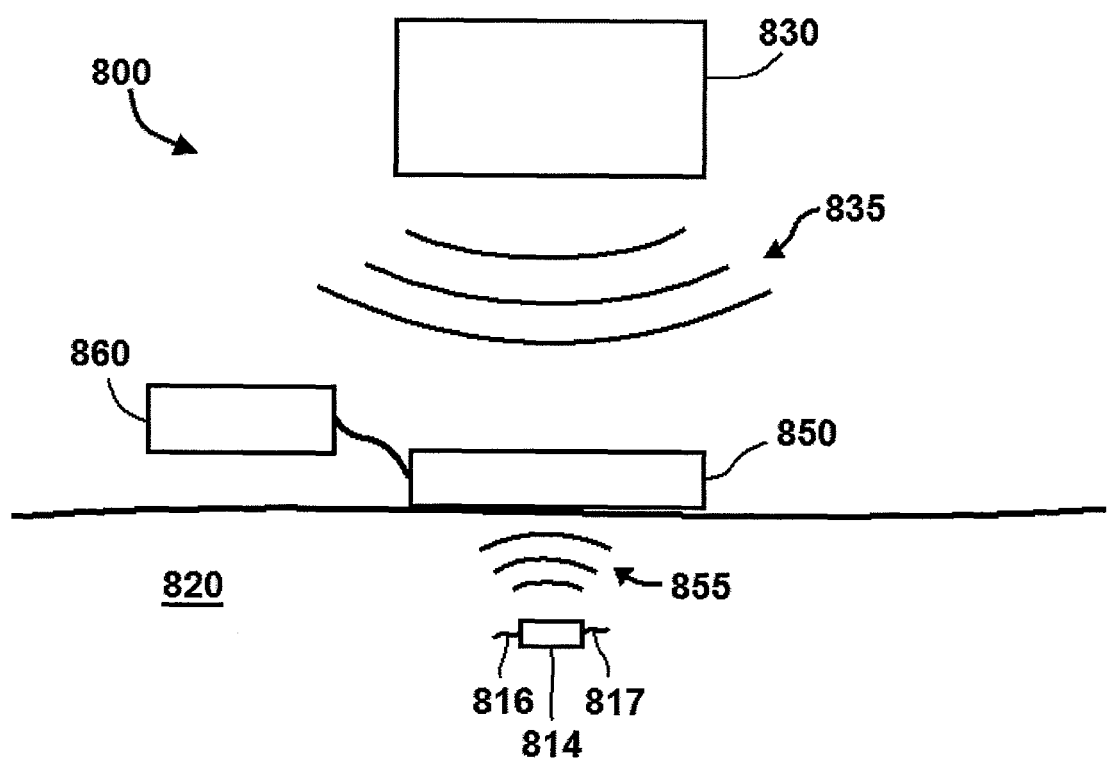
FIG. 8 is a schematic block diagram illustrating one embodiment of a system for providing neurotelemetry.

Referring now to FIG. 8, a system 800 configured to provide neurotelemetry comprises a diode 814 comprising a pair of electrical contacts 816 and 817. It is understood that the components shown in FIG. 8 are not drawn to scale, and that certain components may be enlarged to provide clarity in the illustration. In this embodiment, diode 814 is implanted into electrically-excitable neural tissue 820. A radio frequency exciter 830 is placed proximal to the tissue overlying diode 814 and is configured to emit a radio frequency electrical output 835.

During operation, radio frequency output 835 is modulated with a pulse width and rate. In addition, diode 814 is configured to intermodulate the output of the radio frequency exciter with a bioelectric signal from electrically-excitable neural tissue 820. Diode 814 is further configured to emit an intermodulated signal 855 to a radio receiver 850. System 800 further comprises a demodulator 860 coupled to radio receiver 850. Furthermore, demodulator 860 is configured to demodulate intermodulated signal 855 from diode 814 to detect changes in the amplitude or frequency of radio frequency output 835 from the radio frequency exciter 830.

In certain embodiments, a high frequency signal is applied to the diode from an external RF source constituting a carrier current. Bioelectric currents in parallel with the mixer diode amplitude modulate the applied RF carrier current excitation. When placed in tissue, volume conductivity carries the biopotential modulated carrier current to the surface where it is detected by a second set of surface bioelectrodes or antenna. Demodulation of the detected signal reproduces the original biopotential waveform.

The implanted diode assembly can therefore intermodulate the bioelectrical event on a superimposed high frequency carrier. Over a small change in biopotential, the changes in the carrier current through the diode is reasonably linear. At low drive levels, the diode presents a relatively high source impedance to the electrodes.

In many types of neural monitoring applications, there is a need for multichannel operation to cope with the complexity of functionality of the body. Large electrode arrays systems involving fine wires are used to penetrate tissue to stimulate patterns of neural response particularly in the brain, eye, and auditory prostheses.

It is noted that using a lower amplitude of microwave, instead of applying a relatively strong source of microwave radiation to the implant site, causes the diode to act differently. Microwave currents driven through tissues combine with the natural ionic currents flowing in tissue and do not stimulate tissues by its electrical current flow, but rather intermodulates with local tissue biopotentials at the diode.

The passage of a small but high frequency electrical current flow induced in tissue from an external source combined with a demodulation process on the re-radiated frequencies created by the intermodulation process with the diode, allows one to reconstruct the waveform of the original bioelectrical event that was flowing locally in the tissue and present electrically across the diode-tissue contacts. By demodulating intermodulation components as is known in radio communications, a user is able to remotely record the modulating biopotential signal amplitude.

This approach may provide an improvement over methods in the prior art which use resonant circuits coupled with varactor diodes or other voltage sensing devices of varying sorts. One advantage may be an increased ability to miniaturize the implanted device.

Specific embodiments comprise the use of multiple diodes of micrometer-order in size by methods well known to the art of semiconductor manufacturing. In specific embodiments, the diodes can be introduced into a host by way of a carrier fluid, which can allow the diodes to be distributed more easily through a larger volume of a tissue or at specific points where the diodes are placed. Diodes which are aligned with the electric current flow will forward conduct on one phase of the AC cycle and be passive on the next phase. While it may be desirable for efficiency to have all of the diodes aligned in a common direction, it is not a requirement as long as a sufficient fraction are aligned to produce a sufficiently strong rectification of the current flow.

In certain embodiments, the functionality of a diode can be achieved in multiple ways including that of the use of commercially available semiconductor diodes. Other embodiments may comprise diodes created using microscopic combinations of two different metals separated by a thin insulating layer. Such configurations may be accomplished, for example, by silver copper-oxide copper layering as known to those skilled in the art. Other embodiments may comprise silver and its chloride in combination with other less reactive metals such as platinum or gold. Such diodes can be made essentially any size including as a fine dispersion in a biocompatible fluid transfer medium. Similar diode effects can be achieved using organic semiconductors. In particular, it is known that the organic polypyrrole is an electrical semiconductor, and when doped by various ions, it acquires either p-type or n-type characteristics. A diode can therefore be farmed by the junction of organic materials.

As before, it will be apparent to those skilled in the art that detection and demodulation of both the fundamental as well as harmonics of the carrier wave are possible in a process to demodulate the bioelectric waveform.

It is noted that the efficiency of the diode in intermodulating the carrier wave with the bioelectrical events is determined by the specific characteristics of the diode. Zero bias Shottky diodes for example, require no DC bias offset in their operation while other diodes may require de bias of varying degrees depending on their manufacture.

Depending on the selection of the diode and its electrical characteristics, it is possible to be somewhat selective as to which of a series of diodes introduced at varying depths in tissue contribute to the detected intermodulation of the applied carrier by way of observing that there is an optimum dc bias which produces the greatest possible intermodulation. If the dc bias level is either too high or too low, the intermodulation of a given diode will be relatively little. A series of diodes disposed within tissue for example, can be somewhat individually addressed and their contribution to the overall demodulated signal maximized by applying a dc bias level to the skin along with the carrier frequency. Diodes at some middle position in the tissue will receive an optimal DC bias due to the attenuation of the bias level with depth and so providing an optimum electrical operating condition at that point. Likewise if the bias level is ramped over time there may be a sequential reading the diodes relative to their increasing position of depth in the tissue.

The basic electronic design employs an unusually different approach to energy transfer to miniature medical bioelectronic implants as compared to the current art. High frequency (GHz microwave range) electric fields can be shown to interact in unexpected ways with simple semiconductor diode chips when they are placed near or within biologically-excitable tissues.

The design principle allows simple wireless transmission of electrical power over short ranges to an implanted chip to the extent that it can produce therapeutic neurostimulation. Some embodiments of the invention also excite the same implanted chip so that it acts as a transmitter and thus provides telemetry of bioelectrical and sensor signals from tissues. One embodiment is a compact cell-phone like receiver placed near the skin surface.

Thus, embodiments of the present invention teach a method and design that can do the complementary tasks of both neurostimulation and neurorecording. Embodiments of the present invention allow a substantial reduction in the complexity, size, and bulk of implanted microelectronic neurostimulation/neurotelemetry devices to the degree where some prototypes fit through the lumen of common syringe needles.

REFERENCES

The following references, to the extent that they provide exemplary procedural or other details supplementary to those set forth herein, are specifically incorporated herein by reference.

1. Heetderks, W. "RF Powering Of Millimeter- and Submillimeter-Sized Neural Prosthetic Implants" IEEE Transactions on Biomedical Engineering, Vol. 35, No. 5, 323. May 1988.
2. K. D. Wise, D. J. Anderson, J. F. Hetke, D. R. Kipke, K. Najafi, Wireless Implantable Microsystems: High-Density Electronic Interfaces To The Nervous System Proceedings Of The Ieee, Vol. 92, No. 1, January 2004
3. P. Mohseni, K. Najafi, S. J. Eliades, And X. Wang, "Wireless Multichannel Biopotential Recording Using An Integrated Fm Telemetry Circuit", Ieee Ieee Transactions On Neural Systems And Rehabilitation Engineering, Vol. 13, No. 3, September 2005
4 G. L. Matthaei, "A Study of the Optimum Design of Wide-Band Parametric Amplifiers and Up converters Up Converters", IRE Transactions on Microwave Theory Tech. Vol. MTT-10, pp. 23-28 Jan. 1961.
5. E. Sard, B. Peyton, S. Okwit, "A positive resistance up-converter for ultra-low noise amplification" IEEEE Trans. Micro Theory Techvol. 14, pp. 608-618, December 1966.
6. Towe, B. C., "Passive Biotelemetry by Frequency Keying", IEEE Transactions on Biomedical Engineering, vol. BME-33, no. 10, October 1986.
7. J. Patrick Reilly, Applied Bioelectricity: From Electrostimulation to Electropathology, Springer Verlag., New York, 1998.

The invention claimed is:

1. A method of providing neurostimulation, the method comprising:
   implanting a diode having two nodes into biological tissue such that the nodes of the diode are directly electrically coupled to excitable neural tissue and at least one node of the diode forms an antenna;
   providing a radio frequency exciter proximal to tissue overlying the diode, wherein the radio frequency exciter is configured to emit a radio frequency electromagnetic output;
   modulating the radio frequency electromagnetic output with a pulse width and rate;
   varying the power level of the radio frequency exciter; and
   creating a pulsed current flow from the diode by receiving the modulated radio frequency electromagnetic output with the antenna, wherein the pulsed current flow is sufficient to provide neurostimulation of the excitable neural tissue.

2. The method of claim 1 wherein the nodes are electrically coupled to a dipole.

3. The method of claim 2 wherein the dipole is between 1 millimeter and 1 centimeter in length.

4. The method of claim 2 wherein the dipole is between 1 centimeter and 5 centimeters in length.

5. The method of claim 1 wherein the biological tissue comprises brain tissue, muscle tissue, or nervous system tissue.

6. The method of claim 1 wherein the diode is a semiconductor diode.

7. The method of claim 1 wherein radio frequency exciter is configured to emit radio waves in the microwave frequency range.

8. The method of claim 1 wherein radio frequency exciter is configured to emit radio waves at a frequency between 100 MHz to 8 GHz.

9. The method of claim 1 wherein the radio frequency output is modulated so that it is pulsed for a time period between 100 microseconds and 10 milliseconds and so that it is pulsed in the range of 1 to 200 pulses per second.

10. The method of claim 1 wherein the diode is configured to rectify the radio frequency output from the radio frequency exciter.

11. The method of claim 1 wherein the diode is configured to be placed in the lumen of an 18 gauge needle.

12. The method of claim 1 wherein the diode is arranged in a bridge configuration with additional diodes.

13. A neurostimulation system comprising:
a radio frequency exciter configured to emit a microwave frequency electromagnetic output; and
a diode having two nodes, the diode configured to receive the microwave frequency electromagnetic output from the radio frequency exciter by using at least one of its nodes as an antenna such that the node is configured to be directly electrically coupled to excitable neural tissue, and to rectify the microwave frequency electromagnetic output to provide a pulsating and monopolar current, wherein the pulsating and monopolar current is sufficient to provide neurostimulation of excitable neural tissue.

14. The neurostimulation system of claim 13 wherein the radio frequency exciter is configured to emit radio waves at a frequency between 100 MHz to 8 GHz.

15. The neurostimulation system of claim 13 further comprising an electrical switch in parallel or series with the diode.

16. The neurostimulation system of claim 15 wherein the switch comprises a polymer material loaded with a finely dispersed particulate conductive phase.

\* \* \* \* \*